US00PP15150P2

(12) United States Plant Patent
Olesen et al.

(10) Patent No.: US PP15,150 P2
(45) Date of Patent: Sep. 14, 2004

(54) ROSE PLANT NAMED 'POULAC018'

(50) Latin Name: *Rosa hybrida*
Varietal Denomination: POULac018

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,159

(22) Filed: Dec. 16, 2003

(51) Int. Cl.[7] ..... A01H 5/00
(52) U.S. Cl. ..... Plt./148
(58) Field of Search ..... Plt./148

*Primary Examiner*—Kent Bell
*Assistant Examiner*—S. B. McCormick

(57) ABSTRACT

A new garden rose plant of the compact floribunda class which has abundant, light pink flowers and attractive foliage. This new and distinct variety has shown to be uniform and stable in the resulting generations from asexual propagation.

1 Drawing Sheet

Botanical classification: Rosa hybrida.
Variety denomination: 'POULac018'.

The present invention constitutes a new and distinct variety of garden rose plant which originated from a controlled crossing between a female parent, 'POULnil', described and illustrated in U.S. Plant Pat. No. 13,301 issyed Dec. 3, 2002, and the male parent, an unnamed seedling. The two parents were crossed during the summer of 1999 and the resulting seeds were planted in a controlled environment in Fredensborg, Denmark. The new variety is named 'POULac018'.

The new variety may be distinguished from its seed parent, 'POULnil' by the following combination of characteristics:

1. The seed parent, 'POULnil' is Orange-Red Group 31A and 31B as sepals unfold. 'POULac018' is Yellow Group 3D with intonations of Orange Group 24C as sepals unfold.
2. While the seed parent, 'POULnil' has an average flower diameter of 65 to 75 mm, 'POULac018' has an average flower diameter of 50 mm.
3. While the seed parent, 'POULnil' has a petalage count 16 to 19 petals. 'POULac018' has a petalage count of 80 petals.

The new variety may be distinguished from its pollen parent, an unnamed plant, by the following combination of characteristics:

1. The pollen parent has light red to pink flowers. The same of 'POULac018' are Red Group 55D to 56D.
2. The pollen parent has a petalage count of 18 to 22 petals, while 'POULac018' has a much larger petal count of 80 petals.

The objective of the hybridization of this rose variety was to create a new and distinct product for the floral industry with unique qualities, such as:

1. Uniform and abundant light pink flowers;
2. Vigorous, but compact growth when propagated both as a budded rose and on its own roots;
3. Disease resistance.

This combination of qualities is not present in previously available commercial cultivars of this type, known to the inventors, and distinguish 'POULac018' from all other varieties of which we are aware.

As part of their rose development program, L. Pernille Olesen and Mogens N. Olesen germinated the seeds from the aforementioned hybridization during winter 1999 and conducted evaluations on the resulting seedlings in a controlled environment in Fredensborg, Denmark.

'POULac018' was selected in the spring 2000 by the inventors as a single plant from the progeny of the aforementioned hybridization.

Asexual reproduction of 'POULac018' by traditional budding and rooted cuttings was first done by L. Pernille and Mogens N. Olesen in their nursery in Fredensborg, Denmark in July, 2000. This initial and other subsequent asexual propagations conducted in controlled environments have demonstrated that the characteristics of 'POULac018' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac018'. Specifically illustrated in the drawing:

FIG. 1.1; Open flower, stem showing open flower, the attachment of leaves, and peduncles;

FIG. 1.2; Flower bud closed and flower buds partially open;

FIG. 1.3; Sepals, receptacle, and peduncle;

FIG. 1.4; Flower petals, detached;

FIG. 1.5; Mature and juvenile leaves;

FIG. 1.6; Bare stem exhibiting thorns.

DETAILED DESCRIPTION OF THE VARIETY

The following is a description of 'POULac018', as observed in its growth in a glasshouse located in Fredensborg Denmark. Observed plants were cultivated for a period of 3 months, grown in 15 cm pots. Color references are made using The Royal Horticultural Society (London, England) Colour Chart, 1995, except where common terms of color are used.

For a comparison, several physical characteristics of the rose variety 'POULhilda', a rose variety from the same inventors described and illustrated in U.S. Plant Pat. No. 12,762 issued on Jul. 9, 2002, are compared to 'POULac018' in Chart 1.

CHART 1

| | 'POULac018 | 'POULhilda' |
|---|---|---|
| Petalage count. | 80. | 95 to 100. |
| Petal Color, Upper Surface | Red Group 55B to 55C; Red Group 55D to 56D in the middle and basal zones. | Red Group 49C in marginal zone, White Group 155D in middle and basal zones. |
| Average flower diameter. | 50 mm. | 48 to 52 mm. |

FLOWER AND FLOWER BUD

Blooming habit: Continuous.

Flower bud:

*Size.*—Upon opening, 23 mm in length from base of receptacle to end of bud.

*Bud form.*—Broad based ovoid.

*Bud color.*—As sepals unfold, petals are Yellow Group 3D with intonations of Orange Group 24C. At ¼ opening petals have a distinct underlay of Red Group 55C. Red Group 55D at marginal zone with Red Group 56D at middle and basal zones.

*Sepals.*—Upper Surface: Color: Green Group 137A to 146A. Lower Surface: Color: Yellow-Green Group 146B. Shape: Sepal apex is cirrhose. Base is flat at union with receptacle. Margins: Strong foliaceous appendages on three of the five sepals. Size: 32 mm (l) by 10 mm (w).

*Receptacle.*—Surface: Smooth. Shape: Urn-shaped. Size: 6 mm (h)×6 mm (w). Color: Yellow-Green Group 144A. Anthocyanin: None observed.

*Peduncle.*—Surface: Smooth. Moderate occurrence of stipitate glands. Length: 40 mm to 45 mm. Color: Yellow Group 144A. Strength: Strong.

*Borne.*—Singularly.

Flower bloom:

*Fragrance.*—Moderate rose scent.

*Duration.*—The blooms have a duration on the plant of approximately 18 days.

*Size.*—Average flower diameter is 50 mm when open.

*Form.*—Deep cup. Shape of flower when viewed from the side: Upon opening, upper part: Flat. Upon opening, lower part: Convex. Open flower, upper part: Flat. Open flower, lower part: Convex.

Petalage: 80 petals under normal conditions with 10 petaloids.

Color: Upon opening, petals:

*Outermost petals.*—Outer side: Red Group 55B to 55C at marginal zone. Intonations of Red Group 55D to 56D in the middle and basal zones. Inner Side: White Group 155A. Intonations of Red Group 56C at margins.

*Innermost petals.*—Outer side: Red Group 55B to 55C at marginal zone. Intonations of Red Group 55D to 56D in the middle and basal zones. Inner Side: White Group 155A. Intonations of Red Group 56C at margins.

Upon opening, basal petal spots:

*Outermost petals.*—Outer side: White Group 155A with intonations of Yellow-Green Group 154D. Inner Side: White Group 155A with intonations of Yellow-Green Group 154D.

*Innermost petals.*—Outer side: White Group 155A. Intonations of Yellow-Green Group 154D. Inner Side: White Group 155A. Intonations of Yellow-Green Group 154D.

After opening, petals:

*Outermost petals.*—Outer side: Red Group 55B to 55C at marginal zone. Intonations of Red Group 55D to 56D at the middle and basal zones. Inner Side: White Group 155A. Intonations of Red Group 56C at petal margins.

*Innermost petals.*—Outer side: Red Group 55B to 55C at marginal zone. Intonations of Red Group 55D to 56D at the middle and basal zones. Inner Side: White Group 155A. Intonations of Red Group 56C at margins.

After opening, basal petal spots:

*Outermost petals.*—Outer Side: Yellow-Green Group 154D to Yellow Group 9C and 9D. Inner Side: Yellow-Green Group 154D to Yellow Group 9C and 9D.

*Innermost petals.*—Outer Side: Yellow-Green Group 154D to Yellow Group 9C and 9D. Inner Side: Yellow-Green Group 154D to Yellow Group 9C and 9D.

General tonality: On open flower Red Group 49B to 49C with intonations of Red Group 36C. No change in the general tonality at the end of the $8^{th}$ day. Afterwards, general tonality is Red Group 36C to 36D.

Petals:

*Petal reflex.*—Absent.

*Size.*—24 mm (l)×23 mm (w).

*Margin.*—Entire.

*Shape.*—Apex and base are rounded.

*Texture.*—Smooth.

*Thickness.*—Average.

*Arrangement.*—Not Formal.

Petaloids:

*Quantity.*—10 to 15.

*Size.*—9 mm in length by 6 mm wide.

*Shape.*—Irregular.

*Color.*—Outer side is Red Group 55B to 55C at marginal zone. Intonations of Red Group 55D to 56D at the middle and basal zones. Inner side is White Group 155A, with intonations of Red Group 56C at margins.

Reproductive organs:

*Pistils.*—Length: 5 mm. Quantity: 27.

*Pollen.*—None observed.

*Anthers.*—Color: Yellow Group 13A. Quantity: 46 (actual count).

*Filaments.*—Color: Yellow Group 5C. Length: 7 mm.

*Stigmas.*—Inferior relative to the length and height of the anthers. Color: Yellow-Green Group 150D.

*Styles.*—Color: Yellow-Green Group 150D.

*Hips.*—None Observed.

PLANT

Plant growth: Moderate, upright to bushy. When grown as a 15 cm pot plant, the average height of the plant itself is 29 cm. Average width is 14 cm.

Stems:

*Color.*—Young wood: Yellow-Green Group 144A. Older wood: Yellow-Green Group 144A.

*Surface texture.*—Young wood: Smooth. Older wood: Smooth.

*Thorns.*—Incidence: 10 thorns per 10 cm of stem. Size: Average length: 6 mm. Color: Greyed-Yellow Group 160B. Shape: Concave.

Plant foliage: Normal number of leaflets on normal leaves in middle of the stem: 5 leaflets.

*Compound leaf size.*—85 mm (l)×47 mm (w).

*Quantity.*—5 compound leaves per 10 cm of stem.

*Color.*—Mature Foliage: Upper Leaf Surface: Green Group 137A. Lower Leaf Surface: Yellow-Green Group 148B to Yellow-Green Group 148C. Juvenile foliage: Upper Leaf Surface: Green Group 137A. Lower Leaf Surface: Yellow-Green Group 148B to Yellow-Green Group 148C.

Plant leaves and leaflets:

*Stipules.*—Size: 7 mm. Color: Green Group 137B. Margins: Finely serrated with few stipitate glands.

*Petiole.*—Length: 8 mm. Color: Green Group 137C. Underneath: Yellow-Green Group 144B. Margins: Stipitate glands present. Anthocyanin: None observed.

*Rachis.*—Color: Green Group 137C. Underneath: Yellow-Green Group 144B. Margins: Stipitate glands present. Length: 20 mm.

*Leaflet.*—Edge: Serrated. Size: 35 mm (l)×36 mm (w). Shape: Base shape is rounded. Apex is acute General leaflet shape is ovate. Texture: Smooth. Arrangement: Odd pinnate. Venation: Reticulate. Glossiness: Matte finish.

Disease resistance: Above average resistance to mildew, rust, black spot, and Botrytis under normal glasshouse growing conditions.

Cold hardiness: The variety 'POULac018' has been found to be cold tolerant to USDA Cold Hardiness Zone 6.

What is claimed is:

1. A new and distinct variety of rose plant of the compact floribunda rose class, substantially as herein illustrated and described as a distinct and novel rose variety due to its abundant light pink flowers, disease resistance, and extended period of bloom.

* * * * *

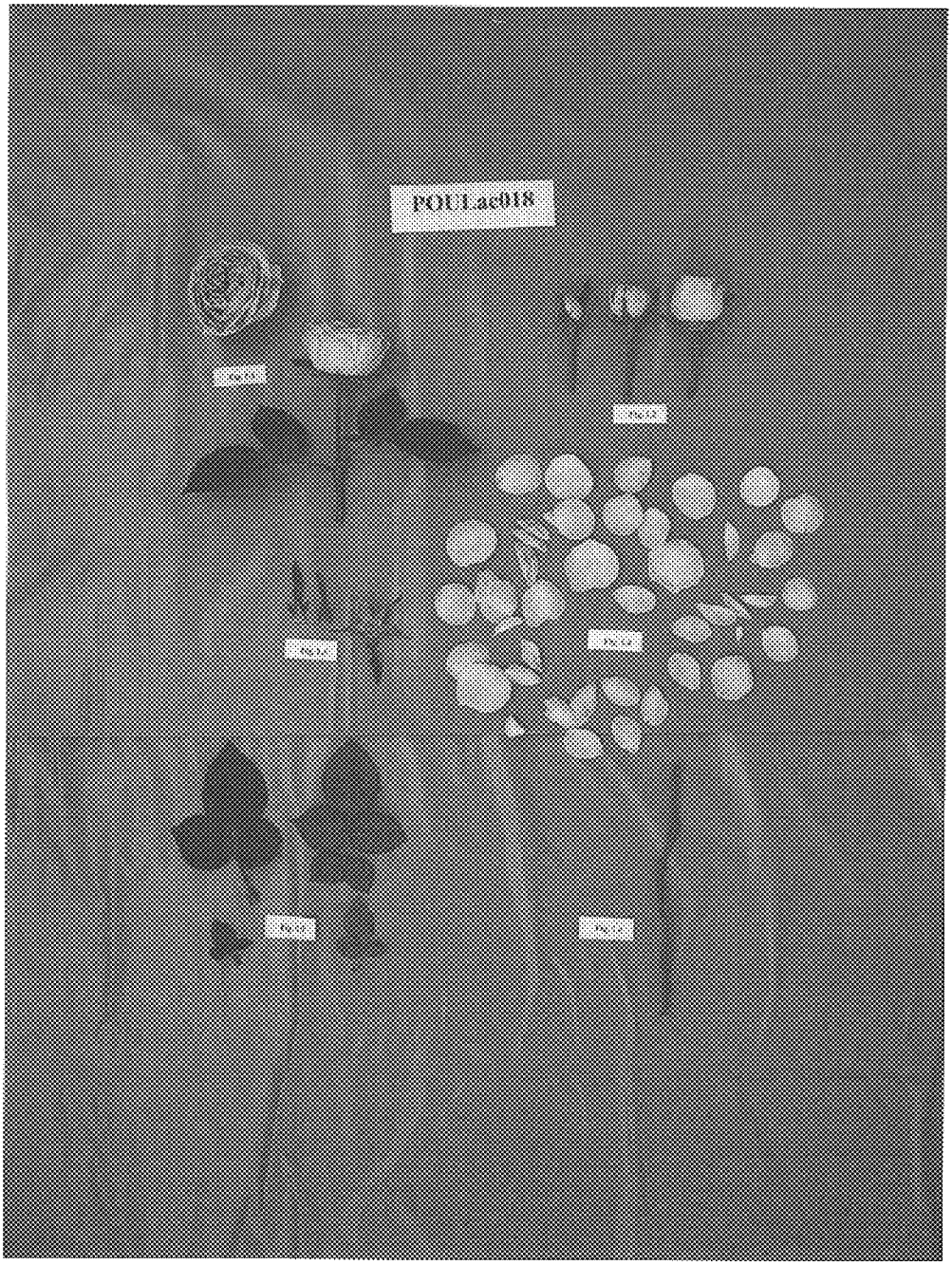
POULac018